US005652263A

United States Patent [19]
Clum et al.

[11] Patent Number: 5,652,263
[45] Date of Patent: Jul. 29, 1997

[54] RETINOID COMPOSITIONS CONTAINING A WATER SOLUBLE ANTIOXIDANT AND A CHELATOR

[75] Inventors: Charles E. Clum, Ewing; Jonas C. T. Wang, Robbinsville, both of N.J.

[73] Assignee: Johnson & Johnson Consumer Products, Inc., Skillman, N.J.

[21] Appl. No.: 674,474

[22] Filed: Jul. 2, 1996

Related U.S. Application Data

[62] Division of Ser. No. 153,543, Nov. 16, 1993, Pat. No. 5,559,149, which is a continuation of Ser. No. 719,264, Jun. 27, 1991, abandoned, which is a continuation-in-part of Ser. No. 471,760, Jan. 29, 1990, abandoned.

[51] Int. Cl.$^6$ ...................................................... A61K 31/19
[52] U.S. Cl. ........................ 514/529; 514/557; 514/703; 514/725; 514/859
[58] Field of Search .................................. 514/529, 557, 514/703, 725, 859

[56] References Cited

U.S. PATENT DOCUMENTS

| | | | |
|---|---|---|---|
| 3,906,108 | 9/1975 | Felty | 514/560 |
| 4,214,000 | 7/1980 | Papa | 514/494 |
| 4,247,547 | 1/1981 | Marks | 514/179 |
| 4,466,805 | 8/1984 | Welters et al. | 8/406 |
| 4,603,146 | 7/1986 | Kligman | 514/559 |
| 4,720,353 | 1/1988 | Bell | 252/309 |
| 4,826,828 | 5/1989 | Wilmott et al. | 514/63 |
| 4,877,805 | 10/1989 | Kligman | 514/381 |

FOREIGN PATENT DOCUMENTS

| | | |
|---|---|---|
| 53-14607 | 5/1978 | Japan . |
| 58-41813 | 3/1983 | Japan . |

OTHER PUBLICATIONS

Dittert, L.W. *Sprowl's American Pharmacy* 7th ed. p. 471 (1974).

*McCutcheon's Emulsifier's and Detergents*, vol. 1, p. 250 (1991).

*Primary Examiner*—Gary E. Hollinden

[57] ABSTRACT

Skin care compositions comprising a water-in-oil emulsion base containing retinoids and possessing good physical and chemical stability.

15 Claims, No Drawings

RETINOID COMPOSITIONS CONTAINING A WATER SOLUBLE ANTIOXIDANT AND A CHELATOR

This is a division, of application Ser. No. 08/153,543, filed Nov. 16, 1993, U.S. Pat. No. 5,559,149 which in turn was a continuation of Ser. No. 07/719,264 filed Jun. 27, 1991, now abandoned, which in turn was a continuation-in-part of Ser. No. 07/471,760 filed Jan. 29, 1990, now abandoned, which are hereby incorporated by reference.

FIELD OF THE INVENTION

This invention relates to skin care compositions containing retinoids which generally improve the quality of the skin, particularly human facial skin. More particularly, the present invention relates to chemically stable skin care compositions comprising a water-in-oil emulsion and certain retinoids and to methods for making such compositions.

BACKGROUND OF THE INVENTION

Skin care compositions containing retinoids have become the focus of great interest in recent years. Retinoic acid, also known as Vitamin A acid or tretinoin, is well-known for the treatment of such skin conditions as acne and products containing retinoic acid are commercially available in various forms from the Dermatological Division of Ortho Pharmaceutical Corporation. Such products, for example, include Retin A* creams, an oil-in-water emulsion of retinoic acid containing as an oil-soluble antioxidant, butylated hydroxytoluene (BHT); Retin A* liquid, a solution of retinoic acid in a polyethylene glycol/ethanol solvent employing BHT as an antioxidant; and Retin A* gel, which comprises retinoic acid in a gel vehicle comprising ethyl alcohol as the solvent, hydroxypropyl cellulose as the thickener or gelling agent and BHT as an antioxidant.

These retinoic acid containing products have proven stable and capable of providing active ingredients after extended periods of storage.

More recently, however, wider use of retinoids has been suggested for treatments other than ache such as, for example, the treatment of skin against photoaging and sun damage. Many individuals who have had a good deal of sun exposure in childhood will show the following gross cutaneous alterations in later adult life: wrinkling, leatheriness, yellowing, looseness, roughness, dryness, mottling (hyperpigmentation) and various premalignant growths (often subclinical). These changes are most prominent in light-skinned persons who burn easily and tan poorly. These cumulative effects of sunlight are often referred to as "photoaging". Although the anatomical degradation of the skin is most advanced in the elderly, the destructive effects of excessive sun exposure are already evident by the second decade. Serious microscopic alterations of the epidermis and dermis occur decades before these become clinically visible. Wrinkling, yellowing, leatheriness and loss of elasticity are very late changes.

The problem of skin aging is addressed in U.S. Pat. No. 4,603,146 wherein Vitamin A acid in an emollient vehicle is suggested as a treatment. Further, in U.S. Pat. No. 4,877,805, it is suggested that a number of retinoids are useful for restoring and reversing sun damage of human skin.

When considering the use of retinoids in skin care products, it is believed that certain retinoids such as, for example, retinol (Vitamin A alcohol), retinal (Vitamin A aldehyde) and retinyl esters such as retinyl acetate and retinyl palmitate would be preferred over retinoic acid. A preferred form is retinol. This is because retinol is an endogenous compound naturally occurring in the human body and essential for good growth, differentiation of epithelial tissues and reproduction. Retinol is also preferred because it has a much larger safety margin than other retinoids such as retinoic acid. Additionally, excess retinol is stored in the human body largely in an inactive ester form, e.g. retinyl palmitate and, to some extent, retinyl acetate. The aldehyde, retinal, also a preferred form, is an active metabolite of retinol and is needed for visual function. Accordingly, attention has turned toward formulating skin care compositions which contain these preferred, naturally occurring retinoids.

In formulating products containing such retinoids, the same properties sought with respect to the retinoic acid formulas are desirable for other retinoid containing compositions. Specifically, much attention is directed toward providing a composition which is aesthetically pleasing and which can deliver active ingredients after a substantial shelf life. Not surprising, in formulating products containing such retinoids, the art is led to the experience gained in the already existing formulas containing retinoic acid. Typically, such formulas comprise oil-in-water emulsions wherein the retinoic acid is carried within the oil phase and is protected from oxidation by employing an oil-soluble antioxidant. With respect to the form of the emulsion, oil-in-water emulsions have been preferred in that, as compared to water-in-oil emulsions for example, they are non-occlusive, non-greasy, compatible with other such emulsion products, easy to remove from the skin and are regarded as more aesthetically pleasing as well as being more economical to manufacture. With respect to chemical stability of the active ingredient, it has been experienced that the retinoic acid in the oil phase is, in the main, well protected by including in such oil phase an oil soluble antioxidant.

Thus, for example, the aforementioned Retin A, cream is an oil-in-water emulsion containing retinoic acid and BHT, an oil-soluble antioxidant. In U.S. Pat. No. 3,906,108 there is disclosed an oil-in-water emulsion of retinoic acid which may include an oil-soluble antioxidant such as BHT or dl-α-tocopherol and a chelating agent e.g. ethylenediaminetetraacetic acid (EDTA). In U.S. Pat. No. 4,466,805, a tanning composition is described which may include, among other ingredients Vitamin A in an oil-in-water emulsion containing Vitamin E and citric acid. In U.S. Pat. No. 4,247,547 still another form of a retinoic acid containing composition, namely a gel, is disclosed and is protected by an antioxidant selected from the group consisting of butylated hydroxytoluene, butylated hydroxyanisole (BHA), ascorbic acid (Vitamin C), propyl gallate, and α-tocopherol (Vitamin E).

The above-described retinoic acid containing compositions have proven to be, or are said to be, chemically stable. Therefore, a number of skin care products have appeared in the marketplace incorporating other retinoids, including for example retinol, retinal and retinyl esters such as retinyl acetate and retinyl palmitate, and these unsurprisingly emulate the formulas of the commercial retinoic acid compositions i.e. are oil-in-water emulsions protected by oil-soluble antioxidants. Unfortunately and unexpectedly, it has been discovered that for reasons not yet clearly understood, the other retinoids in such compositions quickly lose their activity and either oxidize or isomerize to non-efficacious chemical forms with the result that the amount of retinoid actually available to provide the beneficial effects of the product is reduced, in an unacceptably short period of time, to an ineffective quantity and eventually to only trace quantities.

Generally then, products containing retinoids have been limited to oil-in-water emulsions and, with respect to those other than retinoic acid, have suffered from chemical instability. In a few instances, however, products and/or suggestions for products have been made wherein retinoids such as retinol, retinyl acetate and retinyl palmitate are formulated in water-in-oil emulsions.

Thus, for example, in U.S. Pat. No. 4,826,828 it is suggested that a stable composition comprising retinol, retinyl acetate and retinyl palmitate may consist of retinol in a water-in-oil emulsion wherein the emulsion further include two oil-soluble antioxidants, BHT and BHA.

Further, Avon Products, Inc., the assignee of U.S. Pat. No. 4,826,828, sells two skin care products called Bioadvance and Bioadvance 2000. Each of these products is supplied in two bottles, portions of which are mixed together just prior to use. The first bottle contains what is called a "skin lotion", while the second bottle contains what is called a "fortifier". The "skin lotion" is a water-in-oil emulsion having a number of ingredients which include water, emulsifiers, silicone and vegetable oils, preservatives, emollients and butylated hydroxytoluene (BHT). The "fortifier" is a solution which contains a number of ingredients including cyclomethicone (a silicone oil), denatured ethanol, an emulsifier (Polysorbate 20), retinol, retinyl acetate, retinyl palmitate, BHT and BHA. When a specified portion of the "fortifier" is added to a specified portion of the "skin lotion" and mixed, there results a water-in-oil emulsion which comprises retinol, retinyl acetate, retinyl palmitate, BHT and BHA, the latter being oil-soluble antioxidants. The outer package in which Bioadvance is supplied carries a statement which says "Because BIOADVANCE begins to lose effectiveness after one month, for maximum benefits, use a fresh supply each month". It would appear from this statement that the chemical stability of the retinoids in the mixture of the "skin lotion" and the "fortifier" is quite limited. The fact that in both the BIOADVANCE and BIOADVANCE 2000 products the "fortifier" ingredients must be mixed with the "skin lotion" ingredients immediately prior to use indicates that the resulting water-in-oil emulsion which is applied to the skin also has limited chemical stability of one or more of the above-mentioned retinol, retinyl acetate and retinyl palmitate.

Further still, U.S. Pat. No. 4,720,353 to Bell discloses water-in-oil emulsion carriers for various medicaments and drugs intended for topical application to the skin. Water soluble, miscible or dispersible drugs may be incorporated into the aqueous phase of the emulsion. Oil-soluble, miscible or dispersible drugs may be incorporated into the oil phase. Drugs which may be incorporated into the emulsion include derivatives of retinoic acid. Ingredients which may optionally be added to the emulsion include a preservative such as methyl paraben, propyl paraben or imidazolidinyl urea or an antioxidant such as butylated hydroxyanisole and a water or oil soluble vitamin such as vitamin C, tocopherol linoleate and the like.

Still further, EP 0 343 444 A2 to Siemer et al discloses cosmetic preparations based on retinyl palmitate. Example 3 discloses a night cream in the form of an water-in-oil type emulsion comprising retinyl palmitate and butylated hydroxyanisole (BHA). Example 4 discloses a water-in-oil emulsion comprising retinyl acetate and α-Tocopherol (Vitamin E).

Still further, EP 0 330 496 A2 to Batt is directed to skin treatment compositions comprising a topically acceptable base and an effective amount of at least one ester of retinol, said compositions being useful in the treatment of photoaged skin. Example 6 discloses a water-in-oil emulsion comprising Vitamin A propionate and BHT, an oil-soluble antioxidant.

Unfortunately, none of these prior attempts to emulate the stability of the retinoic acid containing compositions have been successful and in each case result in substantial and unacceptable chemical instability of the retinol, retinal or retinoic esters employed therein. Accordingly, there is a need for a composition in which such non-retinoic acid retinoids may be provided in a chemically stable form.

SUMMARY OF THE INVENTION

In accordance with the present invention, it has now been unexpectedly found that certain retinoids may be successfully stabilized against chemical degradation by incorporating them into water-in-oil emulsions comprising a specifically defined stabilizing system. For reasons which are not clearly understood, stability satisfactory for a commercial product has been achievable for certain specific retinoids only by utilizing a specific form of emulsion, i.e. water-in-oil, and then, only by employing a specific stabilizing system.

The retinoids which can be stabilized against chemical degradation in accordance with the principles of the present invention are retinol (Vitamin A alcohol), retinal (Vitamin A aldehyde), retinyl acetate, retinyl palmitate and mixtures thereof.

As used herein, the "chemical stability" or "stability" of a retinoid is defined in terms of the percentage of the specified retinoid which is retained in its original chemical form after the composition has been stored for a specified period of time at a specified temperature. Thus, if the original concentration of all-trans retinol in an absolute ethanol solution were 0.20% by weight and, after two (2) weeks storage at room temperature (21° C.±1° C.), the concentration of all-trans retinol were 0.18% by weight, then the original solution of all-trans retinol in absolute ethanol would be characterized as having a chemical stability of retinol of 90% after two weeks storage at room temperature. In the same fashion, if an emulsion comprising all-trans retinol had an initial concentration of 0.30% by weight and after storage for 13 weeks at 40° C. had a concentration of all trans-retinol of 0.24% by weight, then the original emulsion would be characterized as having a chemical stability of retinol of 80% after 13 weeks storage at 40° C.

Specifically, a commercially usable composition should exhibit a stability of at least about 60% of the active retinoid(s) after 13 weeks storage at 40° C. Preferably such compositions further exhibit a stability of at least about 80% after 13 weeks storage at room temperature.

It has been discovered that, for the specific retinoids which are the subject of this invention only the specific emulsion form, in combination with the selection of a stability system from those described herein, will produce such commercially stable compositions.

Accordingly there is provided, in accordance with the teachings of the present invention, a skin care composition comprising a water-in-oil emulsion and a retinoid selected from the group consisting of retinol, retinal, retinyl acetate, retinyl palmitate and mixtures thereof, said composition further comprising a stabilizing system selected from the group consisting of:

a) a chelating agent and at least one oil-soluble antioxidant;

b) a chelating agent and at least one water-soluble antioxidant; and c) antioxidant present in each of the oil and water phases of said emulsion;

said composition retaining at least about 60% of said retinoids after 13 weeks storage at 40° C.

In a preferred embodiment of the invention, the skin care composition includes one of the aforementioned retinoids, a chelating agent, a water-soluble antioxidant and an oil-soluble antioxidant. Further, in a preferred embodiment of the invention, the composition retains at least about 90% of such retinoids after 13 weeks storage at 21° C.

DETAILED DESCRIPTION OF THE INVENTION

As described above, the composition of the invention is in the form of a particular type of emulsion, namely water-in-oil. As used herein, the generally accepted concept of an emulsion applies i.e., an intimate mixture of two immiscible liquids which remains unseparated for an acceptable shelf life (is physically stable) at or about room temperature. Ordinarily, when two immiscible liquids are mechanically agitated, both phases initially tend to form droplets. Thereafter, when the agitation ceases, the droplets quickly coalesce, and the two liquids tend to separate. On the other hand, an emulsion may be formed and physically stabilized and the lifetime of the droplets in intimate mixture materially increased if a compound, referred to as an emulsifier, is added to the immiscible liquids. Usually only one phase persists in droplet form for a prolonged period of time, and this is referred to as the internal phase which is surrounded by an external phase. An oil-in-water emulsion is one in which the external phase (also called the continuous phase) comprises water and the internal phase (also called the discontinuous or disperse phase) comprises an oil. A water-in-oil emulsion is one in which the external phase comprises an oil and the internal phase comprises water.

Most commercial skin care compositions such as the ones containing retinoic acid are oil-in-water emulsion systems. In accordance with the teaching herein it has been discovered that, in such oil-in-water emulsion systems, certain retinoid compounds, in particular, retinol, retinal, and the retinyl esters tend to be chemically unstable, i.e. they degrade, either by way of oxidation or isomerization, and are, therefore, not available to perform in their desired manner. While this is not clearly understood, it is believed that this degradation occurs as a result of the rapid diffusion of oxygen through the external water phase to the internal oil phase containing the retinoid, and degradation of the retinoid then occurs. Since the diffusion of oxygen is greater in a water phase than an oil phase, an oil-in-water system is more prone to such degradation. Precisely why this occurs for certain selected retinoids and not for others, is not yet understood.

The present invention has overcome these difficulties and instead, provides a water-in-oil emulsion composition containing at least one retinoid compound wherein the physical stability of the emulsion and the chemical stability of the active ingredients is excellent.

As described above, the composition of this invention employs a chemical stabilizing system selected from the group consisting of a) a chelating agent and at least one oil-soluble antioxidant;

b) a chelating agent and at least one water-soluble antioxidant; and c) antioxidant present in each of the oil and water phases of said emulsion;

The water-soluble antioxidants which are useful in the compositions of the present invention include ascorbic acid, sodium sulfite, sodium metabisulfite, sodium bisulfite, sodium thiosulfite, sodium formaldehyde sulfoxylate, isoascorbic acid, thioglycerol, thiosorbitol, thiourea, thioglycolic acid, cysteine hydrochloride, 1,4-diazobicyclo-(2,2,2)-octane and mixtures thereof as well as any other known water-soluble antioxidant compatible with the other components of the compositions.

The oil-soluble antioxidants which are useful in the compositions of the present invention include butylated hydroxytoluene (BHT), ascorbyl palmitate, butylated hydroxyanisole (BHA), α-tocopherol, phenyl-α-naphthylamine, hydroquinone, propyl gallate, nordihydroguiaretic acid, and mixtures thereof as well as any other known oil-soluble antioxidant compatible with the other components of the compositions.

The antioxidants should be utilized in a stabilizing effective amount and may range in total from about 0.001 to 5.0% based on the weight of the total composition, preferably from about 0.01 to 1.0%. The amount of antioxidants selected, the amount of and specific retinoid antioxidants utilized in the compositions of the present invention is dependent in part on the specific being protected and the processing conditions.

In certain aspects of this invention, the compositions include a chelating agent. The retinoid compounds of this invention are sensitive to metal ions and in particular to bi- and tri-valent cations and in certain instances, appear degrade rapidly in their presence. The chelating agent forms a complex with the metal ions thereby inactivating them and preventing them from affecting the retinoid compounds. Chelating agents which are useful in the compositions of the present invention include ethylenediamine tetraacetic acid (EDTA) and derivatives and salts thereof, dihydroxyethyl glycine, citric acid, tartaric acid, and mixtures thereof. The chelating agents should be utilized in a stabilizing effective amount and may range from about 0.01 to 2.0% based on the weight of the total composition, preferably from about 0.05 to 1.0%.

The retinoid compounds which are useful in the compositions of the present invention consist of Vitamin A alcohol (retinol), Vitamin A aldehyde (retinal and Vitamin A esters (retinyl acetate and retinyl palmitate). These retinoids are utilized in the compositions of the present invention in a therapeutically effective amount that may range from about 0.001 to 5.0% by weight of the total compositions, preferably from about 0.001 to 1.0%.

The skin care compositions of the present invention comprising a water-in-oil emulsion can be in the format of cream or lotion formulations, as desired, by varying the relative quantities of the oil and water phases of the emulsion. The pH of the compositions should be in the range of from about 4 to about 9, and preferably from about 4 to about 7.

Minerals oils, animal oils, vegetable oils and silicones have all been used in cosmetic creams and lotions of the emulsion type. In addition to such oils, other emollients and surface active agents have been incorporated in the sucrose distearate, sorbitan triolate, polyoxyethylene (1) monostearate, glycerol monooleate, sucrose distearate, polyethylene glycol (50) monostearate, octylphenoxypoly (ethyleneoxy) ethanol, decaglycerin penta-isostearate, sorbitan sesquioleate, hydroxylated lanolin, lanolin, triglyceryl diisostearate, polyoxyethylene (2) oleyl ether, calcium stearoyl-2-lactylate, methyl glucoside sesquistearate, sorbitan monopalmitate, methoxy polyethylene glycol-22/ dodecyl glycol copolymer(Elfacos E200), polyethylene glycol-45/dodecyl glycol copolymer(Elfacos ST9), polyethylene glycol 400 distearate, and lanolin derived sterol extracts, glycol stearate and glyceryl stearate; alcohols, such as cetyl alcohol and lanolin alcohol; myristates, such as isopropyl myristate; cetyl palmitate; cholesterol; stearic acid; propylene glycol; glycerine, sorbitol and the like. Thickeners such as natural gums and synthetic polymers, as well as preservatives such as methylparaben, butyl paraben, propylparaben and phenoxyethanol, coloring agents and fragrances also are commonly included in such compositions. Other active ingredients such as sunscreen materials and antimicrobial materials may be utilized in the compositions of the present invention provided that they are physically and chemically compatible with the other components of the compositions.

The essence of the present invention is not within the specific composition per se of the cream or lotion formulation, and any of the many formulations or compositions of the cream or lotion type currently utilized in skin care preparations can be employed provided that it is in a water-in-oil emulsion and is chemically compatible with the retinoid compounds. The ratio of the oil phase of the emulsion to the water phase can be from about 5:95 to 99:1. The actual ratio of two phases will depend on the desired final product.

The compositions of the present invention can be prepared by well-known mixing or blending procedures. Each phase of the emulsion is preferably separately prepared with all of the components contained in the appropriate phase except it is usually preferred to omit the retinoid compound. The emulsion is then formed normally by adding the water phase to the oil phase with agitation, and often the emulsion is cooled down when the retinoid compound is added. It is preferred that the portions be prepared under an oxygen depleted atmosphere such as a nitrogen or argon gas blanket. Commercially, it is envisioned that such oxygen depleted atmosphere may be obtained by operating under vacuum conditions and that the product be stored, prior to use, in blind-end containers, preferably aluminum tubes.

The advantages of the invention and specific embodiments of the skin care compositions prepared in accordance with the present invention are illustrated by the following examples. It will be understood, however, that the invention is not confined to the specific limitations set forth in the individual examples, but rather to the scope of the appended claims.

EXAMPLE I (Comparative)

Three oil-in-water emulsions of retinol (Vitamin A alcohol) were prepared having the % w/w compositions set forth in Table 1. These emulsions were prepared according to the following procedure. The ingredients shown under the heading "Aqueous Phase Ingredients" were added to a first glass container equipped with a stainless steel stirrer and heated with stirring to 75°–85° C. under an argon gas blanket. The ingredients shown under the heading "Oil Phase Ingredients" were added to a second glass container equipped with a stainless steel stirrer and heated with stirring to about from 85° to 90° C. under an argon blanket. The ingredients shown under the heading "Retinoid Mixture" were added to a third glass container equipped with a stainless steel stirrer and stirred at room temperature under a blanket of argon gas. Stirring was continued in all instances until uniformity was achieved. The Aqueous Phase Ingredients at 75°–85° C. were then added to the Oil Phase Ingredients. During this addition step, the Oil Phase Ingredients were maintained at 85°–90° C. with stirring under an argon gas blanket. The mixture of the Aqueous Phase Ingredients and Oil Phase Ingredients was stirred, at a temperature in the range of 85°–90° C. and under the argon gas blanket until a uniform oil-in-water emulsion was obtained. After the resulting emulsion was cooled to about 50°–53° C., the Retinoid Mixture was added with stirring. The emulsion was blanketed under argon gas and the temperature was maintained at about 50°–53° C. during the addition of the Retinoid Mixture. After the addition of the Retinoid Mixture was complete, the emulsion was gradually cooled, with stirring and under an argon blanket, to room temperature (approximately 21° C.). The finished emulsion was then transferred under argon gas blanketing to blind end aluminum tubes (2 ounce size) which were promptly crimped and tightly capped. The closed tubes were then set aside for determination of retinol stability after storage for various time periods at various temperatures. Retinol degrades under the influence of UV light. Accordingly, care must be taken at all stages of the emulsion preparation process to protect the retinol from exposure to UV light. This can be accomplished by turning out the lights in the processing area or by conducting the various handling and processing steps under yellow light.

TABLE 1

| Sample Designation | A | B | C |
| --- | --- | --- | --- |
| Aqueous Phase Ingredients | | | |
| Water, q.s. 100% | — | — | — |
| Propylene Glycol | 4.00 | 4.00 | 4.00 |
| Carbomer 934 | 0.50 | 0.50 | 0.50 |
| Oil Phase Ingredients | | | |
| Mixture A | 8.75 | 8.75 | 8.75 |
| Polysorbate 61 (Tween 61) | 1.20 | 1.20 | 1.25 |
| Dimethicone | 1.00 | 1.00 | 1.00 |
| Sorbitan Stearate | 0.80 | 0.80 | 0.80 |
| Retinoid Mixture | | | |
| Ascorbic Acid | 0.00 | 0.00 | 0.10 |
| EDTA | 0.00 | 0.10 | 0.10 |
| Benzyl Alcohol | 0.30 | 0.30 | 0.30 |
| 50% NaOH, q.s. pH 4.7 | — | — | — |
| Methyl Paraben | 0.15 | 0.15 | 0.15 |
| Propyl Paraben | 0.10 | 0.10 | 0.10 |
| Butyl Paraben | 0.05 | 0.05 | 0.05 |
| BHT | 0.02 | 0.02 | 0.02 |
| Fragrance | 0.25 | 0.25 | 0.25 |
| Retinol (all trans), USP | 1.00 | 0.86 | 0.86 |
| Emulsion Type | o/w | o/w | o/w |

In the above Table 1, the ingredient in the Oil Phase Ingredients designated as Mixture A consisted of 1.50 g myristyl myristate; 1.25 g oleic acid (Emersol 228); 1.25 g glyceryl stearate (Emerest 2400); 1.25 g stearic acid (Emersol 132); 1.00 g isopropyl palmitate; 1.00 stearoxytrimethylsilane (Dow Corning 580 Wax); 0.50 synthetic beeswax; 0.50 g stearyl alcohol; and 0.50 g cetyl alcohol. Mixture A was prepared by mixing the indicated ingredients in a glass container, stirring with heat until all ingredients were liquified and uniformly mixed; pouring the liquified mixture into shallow containers; and allowing the mixture to cool to ambient temperature.

Concentrations of all-trans retinol in oil-in-water samples A, B and C in Table 1 were determined after storage for various time periods at various temperatures. Concentrations of retinol and other retinoids such as retinal (vitamin A aldehyde), retinyl acetate and retinyl palmitate can be determined by any suitable analytical procedure. As reported herein, we determined retinoid concentrations by a high performance liquid chromatography (HPLC) procedure in which the chromatograph was equipped with a reversed phase 5 micron C-8 column (25 cm in length×4.6 mm in diameter) and a UV detector at 340 nm. The sample to be analyzed was diluted with a solution of 50% by weight methanol and 50% by weight ethyl acetate to a concentration of 18 micrograms/ml and the retinoid was detected at 340 nm. The gradient mobile phase consisted of an organic portion composed of 5 percent tetrahydrofuran in acetonitrile and an aqueous portion consisting of 0.05N ammonium acetate. The solvent program has an initial composition of 70% organic/30% aqueous which increases linearly to 80% organic/20% aqueous at 13 minutes, then again increases linearly to 100% organic at 15 minutes, where it stays until 19 minutes. After injecting 15 microliters of sample solution into the chromatograph, the analytical conditions were run at a flow rate of 2 ml/min and thermostatically regulated at 40° C. The retention time of retinol (Vitamin A alcohol) is about 6.4 minutes. The retention times of retinal (Vitamin A aldehyde), retinyl acetate, and retinyl palmitate are about 7.5 mins., 10.1 mins. and 18.7 mins., respectively. The HPLC results were found to be reproducible to better than a 3% range of standard deviation.

The results were as follows:

For Sample A: After twenty-six (26) weeks aging at room temperature (21° C.±1° C.), only 39% of the original amount of all-trans retinol was found in the emulsion. After twenty-six (26) weeks aging at 40° C., only three percent (3%) of the original amount of all-trans retinol was found in the emulsion. It is concluded that an oil-in-water emulsion comprising retinol and butylated hydroxytoluene (BHT), an oil-soluble antioxidant, does not have acceptable retinol chemical stability.

For Sample B: After thirteen (13) weeks aging at room temperature, 87% of the original amount of all-trans retinol was found in the emulsion. After thirteen (13) weeks aging at 40° C., just four percent (4%) of the original amount of all-trans retinol was found in the emulsion. After thirteen (13) weeks aging at 50° C., no amount of all-trans-retinoic acid was detected in Sample B. After twenty-six (26) weeks aging at room temperature, fifty-seven percent (57%) of the original amount of all-trans retinol was found in the emulsion. It is concluded that chemical stability of all-trans retinol in an oil-in-water emulsion comprising all-trans retinol, BHT and disodium EDTA (a chelating agent) does not have acceptable chemical stability.

For Sample C: After thirteen (13) weeks aging at room temperature, sixty percent (60%) of the initial amount of all-trans retinol was found in the emulsion, while after thirteen (13) weeks aging at 40° C. twenty-three percent (23%) all-trans retinol was detected. No amount of all-trans retinol was detected after Sample C was stored for thirteen (13) weeks at 50° C.

After twenty-six (26) weeks aging at room temperature, forty-two percent (42%) of the initial amount of all-trans retinol was found in Sample C; after fifty-two (52) weeks aging at room temperature, thirty-one percent (31%) of the initial concentration of all-trans retinol remained in Sample C.

From the foregoing aging results, it is concluded that the chemical stability of all-trans retinol in an oil-in-water emulsion comprising all-trans retinol, an oil-soluble antioxidant (BHT), a water-soluble antioxidant (ascorbic acid) and a chelating agent (ethylenediaminetetraacetic acid) is commercially unsatisfactory.

EXAMPLE II

Five water-in-oil (w/o) emulsions of retinol (Vitamin A alcohol) were prepared having the % w/w compositions set forth in Table 2. These emulsions were prepared according to the following procedure. The ingredients shown under the heading "Oil Phase Ingredients" were added under argon gas blanketing to a suitable sized glass beaker equipped with a stainless steel stirrer and heated with stirring to 80° C. until uniformly mixed. The ingredients shown under the heading "Aqueous Phase Ingredients" were added under argon gas blanketing to a separate glass container equipped with a stainless steel stirrer and heated with stirring to 80° C. until uniformly mixed. The pH of the Aqueous Phase Ingredients was adjusted to 4.7 using 50% NaOH. The Aqueous Phase Ingredients at 80° C. were added to the Oil Phase Ingredients also at 80° C., with agitation to form a water-in-oil emulsion, this addition step also being done under an argon gas blanket. The use of argon gas blanketing was continued through the preparation procedure being described. The water-in-oil emulsion was homogenized and cooled to about 50° C. with stirring. The phenoxyethanol and the fragrance were then added to the emulsion. The retinol was then added to the emulsion which was then gradually cooled until the temperature was below 40° C. The water-in-oil emulsion was transferred under argon gas blanketing to small blind-end aluminum tubes which were promptly crimped and tightly capped. Care was taken at all stages of the emulsion preparation process to protect the retinol from exposure to ultraviolet (U.V.) light. As indicated earlier herein, this can be accomplished by turning out the lights in the processing area or by conducting the various handling and processing steps under yellow light.

TABLE 2

| Sample No. | 1* | 2 | 3* | 4* | 5* |
|---|---|---|---|---|---|
| Aqueous Phase Ingredients | | | | | |
| Deionized Water, q.s. 100% | — | — | — | — | — |
| Sorbitol (70%) | 5.00 | 5.00 | 5.00 | 5.00 | 5.00 |
| Methyl Paraben | 0.30 | 0.30 | 0.30 | 0.30 | 0.30 |
| Ascorbic Acid | 0.00 | 0.10 | 0.00 | 0.00 | 0.10 |
| EDTA | 0.10 | 0.00 | 0.00 | 0.00 | 0.00 |
| Oil Phase Ingredients | | | | | |
| Light Mineral oil | 25.00 | 25.00 | 25.00 | 25.00 | 25.00 |
| Propyl Paraben | 0.20 | 0.20 | 0.20 | 0.20 | 0.20 |
| Elfacos C-26 | 6.00 | 6.00 | 6.00 | 6.00 | 6.00 |
| Elfacos E-200 | 5.00 | 5.00 | 5.00 | 5.00 | 5.00 |
| Elfacos ST-9 | 3.00 | 3.00 | 3.00 | 3.00 | 3.00 |
| Stearoxytrimethyl-silane (Dow Corning 580 Wax) | 1.00 | 1.00 | 1.00 | 1.00 | 1.00 |
| Dimethicone, 50 Cstk | 1.00 | 1.00 | 1.00 | 1.00 | 1.00 |
| BHT | 0.00 | 0.05 | 0.00 | 0.05 | 0.00 |
| Phenoxyethanol (preservative) | 1.00 | 1.00 | 1.00 | 1.00 | 1.00 |
| Fragrance | 0.25 | 0.25 | 0.25 | 0.25 | 0.25 |
| Retinol (all-trans), USP | 0.345 | 0.345 | 0.345 | 0.345 | 0.345 |
| 50% NaOH, q.s. pH = 4.7 | — | — | — | — | — |
| Emulsion Type | w/o | w/o | w/o | w/o | w/o |

*Comparative Examples

The water-in-oil emulsions of Table 2 were stored at 50° C. for periods of one (1) and two (2) weeks and then analyzed by the HPLC technique described earlier herein to determine the amount of retinol remaining in the samples. The results of the analysis were as follows:

| Table 2 Sample No. | Wt. % BHT | Wt. % EDTA | Wt. % Ascorbic Acid | % of Original Amount Of Retinol Remaining After Aging at 50° C. | |
|---|---|---|---|---|---|
| | | | | 1 Week | 2 Weeks |
| 1 | 0.00 | 0.10 | 0.00 | 90 | 65 |
| 2 | 0.05 | 0.00 | 0.10 | 99 | 90 |
| 3 | 0.00 | 0.00 | 0.00 | 75 | 85 |
| 4 | 0.05 | 0.00 | 0.00 | 95 | 85 |
| 5 | 0.00 | 0.00 | 0.10 | 93.5 | 70 |

The following conclusions may be drawn from the above test data:

A water-in-oil emulsion of retinol containing neither an oil-soluble antioxidant, a water-soluble antioxidant nor a chelating agent (Table 2, comparative Sample 3) retained only 75% of its initial amount of retinol after one week aging at 50° C. After two weeks aging at 50° C., the analytical results indicated that 85% of the original amount of retinol remained in comparative Sample 3. This figure of 85% was thought to be inaccurate in view of the fact that only 75% of the original amount of retinol remained after one week aging. In any event, the chemical stability of retinol is poor and this emulsion cannot be considered the basis for a commercial product having acceptable long term chemical stability of retinol.

A water-in-oil emulsion of retinol containing a water-soluble antioxidant (ascorbic acid) but containing neither an oil-soluble antioxidant or a chelating agent (Table 2, comparative Sample 5) was found to retain 93.5% of its original concentration of retinol after one week aging at 50° C. This represented somewhat of an improvement in chemical stability of retinol compared to comparative Sample 3 of Table 2 under the same storage conditions. However, after two weeks storage at 50° C., only 70% of the original amount of retinol remained in comparative Sample 5, Table 2. In view of the rapid fall off and low values comparative Sample 5 of Table 2 cannot be the basis for a commercial product having acceptable long term chemical stability of retinol.

A water-in-oil emulsion of retinol containing an oil-soluble antioxidant (BHT) but containing neither a chelating agent nor a water-soluble antioxidant (Table 2, comparative Sample 4) was found to retain 95% of its original concentration of retinol after one week aging at 50° C. and falls off rapidly to a low value of 85% after two weeks aging at the same temperature. This represents somewhat of an improvement over the chemical stability of retinol in comparative Sample 3 and comparative Sample 5 of Table 2. In view of the rapid decrease in retinol concentrations after two weeks and the relatively low quantity retained as retinol at that time, comparative Sample 4 of Table 2 is not suitable as the basis for a commercial product having acceptable chemical stability of retinol.

A water-in-oil emulsion of retinol containing a chelating agent (i.e. ethylenediaminetetracetic acid, EDTA but neither a water-soluble antioxidant nor an oil-soluble antioxidant (Table 2, Sample 1) was found to retain 90% of its original concentration of retinol after one week aging at 50° C. and 65% after two weeks aging at the same temperature. This is poor chemical stability and emulsion Sample 1 of Table 2 cannot form the basis for a commercial product having acceptable long term chemical stability of retinol.

A water-in-oil emulsion of retinol containing an oil-soluble antioxidant (BHT) and a water-soluble antioxidant (ascorbic acid) but containing no chelating agent (Table 2 Sample 2) was found to retain 99% of its original concentration of retinol after one week aging at 50° C. and 90% after two weeks aging at the same temperature. This is good chemical stability and hence emulsion ample 2 of Table 2 could form the basis for a commercial product having acceptable long term chemical stability of retinol.

To summarize, water-in-oil emulsions containing retinol were found to be unsuitable when no chemical stabilizing system was employed (comparative Sample 3), when only a chelating agent was employed (comparative Sample 1), when only an oil-soluble antioxidant was employed (comparative Sample 4) or when only a water-soluble antioxidant was employed (comparative Sample 5). Surprisingly and for reasons totally unknown to us at this time, when both a water-soluble and an oil-soluble antioxidant were employed (Sample 2), the resulting composition exhibited chemical stability.

EXAMPLE III

Water-in-oil emulsions comprising retinol were prepared having the compositions given in Table 3. These emulsions were prepared by the same general procedure used to prepare the water-in-oil emulsions given in Table 2. After the water phase ingredients were added to the oil phase ingredients as described hereinabove, the remaining ingredients were added to the resulting water-in-oil emulsion in the order set forth in Table 3, with retinol being the last component to be added. As indicated earlier, the emulsions were prepared under argon gas blanketing (other inert gases, e.g. nitrogen or carbon dioxide could be used, if desired) to minimize the possibility of entraining oxygen during the various mixing steps. Measures were taken (as described above) to minimize the exposure of retinol to UV light.

TABLE 3

| Sample No. | 1 | 2 | 3 |
|---|---|---|---|
| Aqueous Phase Ingredients | | | |
| Deionized Water, q.s. 100% | — | — | — |
| Sorbitol, (70%) soln. | 5.00 | 5.00 | 5.00 |
| Methyl Paraben | 0.30 | 0.30 | 0.30 |
| Propyl Paraben | 0.20 | 0.00 | 0.00 |
| EDTA, disodium salt | 0.00 | 0.10 | 0.10 |
| Ascorbic Acid | 0.00 | 0.10 | 0.10 |
| Oil Phase Ingredients | | | |
| Elfacos E-200 | 5.00 | 5.00 | 5.00 |
| Elfacos ST-9 | 3.00 | 3.00 | 3.00 |
| Elfacos C-26 | 5.00 | 6.00 | 6.00 |
| Mineral oil | 25.00 | 25.00 | 25.00 |
| BHT | 0.05 | 0.00 | 0.05 |
| Stearoxytrimethyl-silane (Dow Corning 580 Wax) | 1.00 | 1.00 | 1.00 |
| Dimethicone, 50 Cstk | 1.00 | 1.00 | 1.00 |
| Propyl Paraben | 0.00 | 0.20 | 0.20 |
| Dowicil 200 (preservative) | 0.10 | 0.10 | 0.10 |
| EDTA, disodium salt | 0.10 | 0.00 | 0.00 |
| Fragrance | 0.25 | 0.25 | 0.25 |
| Retinol (Vitamin A alcohol), USP | 0.86 | 0.345 | 0.345 |
| 50% NaOH, q.s. pH = 4.7 | — | — | — |
| Emulsion Type | w/o | w/o | w/o |

The water-in-oil emulsions of Table 3 were stored for various periods of time at various temperatures and then analyzed by the HPLC technique described herein to determine the amount of retinol remaining therein. The results of these tests were as follows:

TEST RESULTS

| Table 3 Sample No | Wt % BHT | Wt % EDTA | Wt % Ascorbic Acid | % of Original Amount of Retinol Remaining After 13 Weeks Aging | | |
|---|---|---|---|---|---|---|
| | | | | 21° C. | 40° C. | 50° C. |
| 1 | 0.05 | 0.10 | 0.00 | 97 | 89 | 83 |
| 2 | 0.00 | 0.10 | 0.10 | 93 | 89 | * |
| 3 | 0.05 | 0.10 | 0.10 | 100 | 96 | 94 |

(* = data not available)

It can be seen from the above Test Results that water-in-oil emulsions comprising retinol, a chelating agent and either a water-soluble antioxidant or an oil-soluble antioxidant retain greater than 90% of their original concentration of retinol after being aged for 13 weeks at room temperature (21° C.). These same emulsions retain at least about 89% of their original concentration of retinol after being aged for 13 weeks at 40° C.

It will further be seen that a water-in-oil emulsion comprising retinol, a chelating agent, a water-soluble antioxidant and an oil-soluble antioxidant (Table 3, Sample 3) was found to retain 100% of its original amount of retinol after 13 weeks aging at room temperature, 96% of the original amount of retinol after 13 weeks aging at 40° C. and 94% of the original amount of retinol after 13 weeks aging at 50° C. The same emulsion was found to retain 97% of its original amount of retinol after 26 weeks storage at 21° C., 92% of its original amount of retinol after 26 weeks storage at 40°, and 95.3% of its original amount of retinol after 52 weeks storage at room temperature.

EXAMPLE IV

Two water-in-oil emulsions, one comprising retinyl acetate and the other comprising retinyl palmitate, were prepared having the % w/w compositions set forth in Table 4, Samples 3 and 4, respectively. These two water-in-oil emulsions were prepared by the same general procedure used to prepare the water-in-oil emulsions shown in Tables 2 and 3.

For comparison purposes, two oil-in-water emulsions, one comprising retinyl acetate and the other comprising retinyl palmitate, were prepared having the % w/w compositions shown in Table 4, comparative Samples 1 and 2, respectively. These two oil-in-water emulsions were prepared by the same general procedure used to prepare the oil-in-water emulsions shown in Table 1.

TABLE 4

| Sample No. | 1* | 2* | 3 | 4 |
|---|---|---|---|---|
| Aqueous Phase Ingredients | | | | |
| Deionized Water, q.s. 100% | — | — | — | — |
| Sorbitol, (70%) soln. | 0.00 | 0.00 | 5.00 | 5.00 |
| Methyl Paraben | 0.15 | 0.15 | 0.30 | 0.30 |
| EDTA, Na$_2$ | 0.10 | 0.10 | 0.10 | 0.10 |
| Ascorbic Acid (AA) | 0.10 | 0.10 | 0.10 | 0.10 |
| Carbopol 934 | 0.50 | 0.50 | 0.00 | 0.00 |
| Propylene Glycol | 4.00 | 4.00 | 0.00 | 0.00 |

TABLE 4-continued

| Sample No. | 1* | 2* | 3 | 4 |
|---|---|---|---|---|
| Oil Phase Ingredients | | | | |
| Elfacos E-200 | 0.00 | 0.00 | 5.00 | 5.00 |
| Elfacos ST-9 | 0.00 | 0.00 | 3.00 | 3.00 |
| Elfacos C-26 | 0.00 | 0.00 | 6.00 | 6.00 |
| Mineral oil | 0.00 | 0.00 | 25.00 | 25.00 |
| BHT | 0.02 | 0.02 | 0.05 | 0.05 |
| Stearoxytrimethyl-silane (Dow Corning 580 Wax) | 0.00 | 0.00 | 1.00 | 1.00 |
| Dimethicone, 50 Cstk | 1.00 | 1.00 | 1.00 | 1.00 |
| Propyl Paraben | 0.10 | 0.10 | 0.20 | 0.20 |
| Butyl Paraben | 0.05 | 0.05 | 0.00 | 0.00 |
| Mixture A | 8.75 | 8.75 | 0.00 | 0.00 |
| Arlacel 60 | 0.80 | 0.80 | 0.00 | 0.00 |
| Tween 61 | 1.20 | 1.20 | 0.00 | 0.00 |
| Dowicil 200 | 0.00 | 0.00 | 0.10 | 0.10 |
| Benzyl Alcohol | 0.30 | 0.30 | 0.00 | 0.00 |
| Fragrance | 0.25 | 0.25 | 0.25 | 0.25 |
| Retinyl Palmitate | 0.00 | 0.64 | 0.00 | 0.76 |
| Retinyl Acetate | 0.397 | 0.00 | 0.45 | 0.00 |
| 50% NaOH, q.s. H = 4.7 | — | — | — | — |
| Emulsion Type | o/w | o/w | w/o | w/o |

*Comparative

In the above Table 4, Mixture A consisted of 1.50 g myristyl myristate; 1.25 g oleic acid (Emersol 228); 1.25 g glyceryl stearate (Emerest 2400); 1.25 g stearic acid (Emersol 132); 1.00 g isopropyl palmitate; 1.00 stearoxytrimethylsilane (Dow Corning 580 Wax); 0.50 synthetic beeswax; 0.50 g stearyl alcohol; and 0.50 g cetyl alcohol. Mixture A was prepared by mixing the indicated ingredients in a glass container; stirring with heat until all ingredients were liquified and uniformly mixed; pouring the liquified mixture into shallow containers; and allowing the mixture to cool to ambient temperature.

These four emulsions, after being packed off into closed two-ounce aluminum tubes, were stored for various time periods at various temperatures. The emulsions were analyzed by the previously mentioned HPLC analytical procedure, to determine the amount of retinyl ester present after the various storage periods. The results of the tests were as follows:

TEST RESULTS

| Table 4 Sample No. | Emulsion Type | Wt % BHT | Wt % EDTA | Wt % AA | % of Original Amount of Retinyl Ester Remaining |
|---|---|---|---|---|---|
| 1 | o/w | 0.02 | 0.10 | 0.10 | 1% after 6 days at 50° C. |
| 2 | o/w | 0.02 | 0.10 | 0.10 | 27% after 6 days at 50° C. |
| 3 | w/o | 0.05 | 0.10 | 0.10 | 91% after 13 wks at 21° C. |
| | | | | | 58% after 13 wks at 40° C. |
| | | | | | 16% after 13 wks at 50° C. |
| 4 | w/o | 0.05 | 0.10 | 0.10 | 100% after 13 wks at 21° C. |
| | | | | | 96% after 13 wks at 40° C. |
| | | | | | 85% after 13 wks at 50° C. |
| | | | | | 97.3% after 26 wks at 21° C. |
| | | | | | 90% after 26 wks at 40° C. |
| | | | | | 94% after 52 wks at 21° C. |

As can be seen from the above test results, the oil-in-water emulsion comprising retinyl acetate, BHT, ascorbic acid and EDTA (Table 4, comparative Sample 1) retained only one percent (1%) of its original amount of retinyl acetate after 6 days aging at 50° C. Thus it is seen that the chemical stability of retinyl acetate in the oil-in-water emulsion is very poor. On the other hand, the chemical stability of retinyl acetate was found to be very good in a water-in-oil emulsion comprising retinyl acetate, BHT, ascorbic acid and EDTA (Table 4, Sample 3). The test results show that when retinyl acetate is formulated in the mentioned water-in-oil emulsion, ninety-one percent (91%) of the original amount of retinyl acetate is retained after 13 weeks storage at room temperature (21° C.), fifty-eight percent (58%) of the original amount of retinyl acetate is retained after 13 weeks storage at 40° C. and sixteen percent (16%) of the original amount of retinyl acetate is retained after 13 weeks storage at 50° C.

It can also be seen from the test results that an oil-in-water emulsion comprising retinyl palmitate, BHT, ascorbic acid and EDTA (Table 2, comparative Sample 2) retained just twenty-seven percent (27%) of its original amount of retinyl palmitate after 6 days aging at 50° C. Thus, it is seen that the chemical stability of retinyl palmitate in an oil-in-water emulsion is not satisfactory. In contrast, the chemical stability of retinyl palmitate was found to be excellent in a water-in-oil emulsion comprising retinyl palmitate, BHT, ascorbic acid and EDTA (Table 4, Sample 4 ). As can be seen from the test results, when retinyl palmitate was formulated in the mentioned water-in-oil emulsion, 100%, 96% and 85% of the original amount of retinyl palmitate was retained after 13 weeks aging at room temperature (21° C.), 40° C., an 50° C., respectively. 97.3% and 90% of the original amount of retinyl palmitate was found to be retained after 26 weeks aging at room temperature (21° C.), and 40° C., respectively. 94% of the original amount of retinyl palmitate was found to be retained after 52 weeks aging at room temperature (21° C.).

EXAMPLE V

A water-in-oil cream composition was prepared according to the following procedure. In a suitable sized glass beaker held under argon gas blanketing and fitted with a stainless steel stirrer 250 g mineral oil, 2 g propylparaben, 60 g Elfacos C-26, 50 g Elfacos E200, 30 g Elfacos ST-9, 10 g stearoxytrimethylsilane, 10 g dimethicone (50 cstk), and 0.5 g butylated hydroxytoluene (BHT) were heated to 80° C. and mixed. In a separate glass container, also held under argon gas blanketing and fitted with a stainless steel stirrer, approximately 520 g deionized water, 50 g sorbitol solution 70%, 3 g methylparaben, 1 g disodium edetate and 1 g ascorbic acid were mixed, adjusted to pH 4.7 with dilute sodium hydroxide, heated to 80° C. and then added to the first mixture with agitation and under argon blanketing to form a water-in-oil emulsion. The emulsion was homogenized and cooled to about 50° C. with mixing and maintaining the argon gas blanketing. 1 g Dowicil 200 preservative and 2.5 g fragrance followed by 3.45 g of retinol were added. Deionized water was added to return the batch weight to 1000 g and the batch was mixed under argon gas blanketing until uniform and the temperature was below 40° C. The finished batch was filled into blind-end aluminum tubes under argon gas blanketing and had the following formulation:

| Ingredient | % w/w |
| --- | --- |
| mineral oil | 25.000 |
| hydroxyoctacosanyl hydroxystearate (Elfacos C26) | 6.000 |
| sorbitol solution, 70% | 5.000 |
| methoxy PEG-22/dodecyl glycol copolymer (Elfacos E200) | 5.000 |
| PEG-45/dodecyl glycol copolymer (Elfacos ST9) | 3.000 |
| stearoxytrimethylsilane | 1.000 |
| dimethicone (50 cstk) | 1.000 |
| Vitamin A alcohol (retinol)* | 0.345 |
| methylparaben | 0.300 |
| fragrance | 0.250 |
| propylparaben | 0.200 |
| Quaternium 15 (Dowicil 200) | 0.100 |
| disodium edetate | 0.100 |
| ascorbic acid | 0.100 |
| butylated hydroxytoluene | 0.050 |
| 50% aqueous NaOH | q.s. to pH 4.7 |
| deionized water | q.s. to 100.000 |

*all-trans (USP)

The resulting water-in-oil emulsion was found to retain 100% of its original amount of retinol after 4 weeks aging at room temperature (21° C.). 97.8% of the original amount of retinol was retained after 4 weeks aging at 40° C. and 96.6% of the original amount was retained after 4 weeks agin at 50° C. After 13 weeks aging, the emulsion retained the following percentages of its original amount of retinol: 99.1% at room temperature; 96.2% at 40° C.; and 94% at 50° C. After 26 weeks aging, the emulsion retained the following percentages of its original amount of retinol: 97% at room temperature and 92% at 40° C. This is excellent chemical stability of the retinol.

EXAMPLE VI

A water-in-oil cream composition was prepared in accordance with the procedure of Example V with the amount of retinol being increased to 1.25% w/w and consists of the following ingredients:

| Ingredient | % w/w |
| --- | --- |
| mineral oil | 25.000 |
| hydroxyoctacosanyl hydroxystearate (Elfacos C26) | 5.000 |
| sorbitol solution, 70% | 5.000 |
| methoxy PEG-22/dodecyl glycol copolymer (Elfacos E200) | 5.000 |
| PEG-45/dodecyl glycol copolymer (Elfacos ST9) | 3.000 |
| stearoxytrimethylsilane | 1.000 |
| dimethicone (50 cstk) | 1.000 |
| Vitamin A alcohol (retinol)* | 1.250 |
| methylparaben | 0.300 |
| fragrance | 0.250 |
| propylparaben | 0.200 |
| Quaternium 15 (Dowicil 200) | 0.100 |
| disodium edetate | 0.100 |
| ascorbic acid | 0.100 |
| butylated hydroxytoluene | 0.100 |
| 50% aqueous NAOH | q.s. to pH 4.7 |
| deionized water | q.s. to 100.000 |

*all-trans (USP)

The resulting water-in-oil emulsion retained 93% of its original amount of retinol after aging for 13 weeks at room temperature (21° C.).

EXAMPLE VII

A water-in-oil cream composition was prepared in accordance with the procedure of Example V with 0.5 g propyl gallate replacing the butylated hydroxytoluene and omitting ascorbic acid. The composition consisted of the following ingredients:

| Ingredient | % w/w |
| --- | --- |
| mineral oil | 25.000 |
| hydroxyoctacosanyl hydroxystearate (Elfacos C26) | 5.000 |
| sorbitol solution, 70% | 5.000 |
| methoxy PEG-22/dodecyl glycol copolymer (Elfacos E200) | 5.000 |
| PEG-45/dodecyl glycol copolymer (Elfacos ST9) | 3.000 |
| stearoxytrimethylsilane | 1.000 |
| dimethicone (50 cstk) | 1.000 |
| Vitamin A alcohol (retinol) | 0.345 |
| methylparaben | 0.300 |
| fragrance | 0.250 |
| propylparaben | 0.200 |
| Quaternium 15 (Dowicil 200) | 0.100 |
| disodium edetate | 0.100 |
| propyl gallate | 0.050 |
| butylated hydroxytoluene | 0.000 |
| ascorbic acid | 0.000 |
| 50% aqueous NAOH | q.s. to ph 4.7 |
| distilled water | q.s. to 100.000 |

The resulting water-in-oil emulsion composition was an off-white, water-in-oil cream which was found to retain 91% of its original retinol concentration after 2 weeks aging at room temperature (21° C.), 84.8% after 2 weeks aging at 40° C. and 86.8% after 2 weeks aging at 50° C. The emulsion was found to retain 79% of its original amount of retinol after 8 weeks aging at room temperature (21° C.), 58% after 8 weeks aging at 40° C., and 65% after 8 weeks aging at 50° C. The emulsion was found to retain 77% of its original amount of retinol after 13 weeks aging at room temperature, 78% after 13 weeks aging at 40° C. and 59% after 13 weeks aging at 50° C.

EXAMPLE VIII

A water-in-oil cream composition was prepared in accordance with the procedure of Example V with 0.5 g nordihydroguiaretic acid replacing the butylated hydroxytoluene and omitting the ascorbic acid. The composition consisted of the following ingredients:

| Ingredient | % w/w |
| --- | --- |
| mineral oil | 25.000 |
| hydroxyoctacosanyl hydroxystearate (Elfacos C26) | 5.000 |
| sorbitol solution, 70% | 5.000 |
| methoxy PEG-22/dodecyl glycol copolymer (Elfacos E200) | 5.000 |
| PEG-45/dodecyl glycol copolymer (Elfacos ST9) | 3.000 |
| stearoxytrimethylsilane | 1.000 |
| dimethicone (50 cstk) | 1.000 |
| Vitamin A alcohol (retinol)* | 0.345 |
| methylparaben | 0.300 |
| fragrance | 0.250 |
| propylparaben | 0.200 |
| Quaternium 15 (Dowicil 200) | 0.100 |
| disodium edetate | 0.100 |
| nordihydroguiaretic acid | 0.050 |
| butylated hydroxytoluene | 0.000 |
| ascorbic acid | 0.000 |
| 50% aqueous NaOH | q.s. to pH 4.7 |
| deionized water | q.s. to 100.000 |

*all-trans (USP)

The resulting water-in-oil emulsion composition was found to retain 96.8% of its original amount of retinol after 2 weeks aging at room temperature (21° C.), 87.6% after 2 weeks aging at 40° C. and 91.2% after 2 weeks aging at 50° C. The composition was found to retain 91.2% of its original amount of retinol after 8 weeks aging at room temperature, 72.6% after 8 weeks aging at 40° C. and 50.8% after 8 weeks aging at 50° C. The composition was found to retain 91.6% of its original amount of retinol after 13 weeks aging at room temperature, 69.0% after 13 weeks aging at 40° C., and 59.3% after 13 weeks aging at 50° C.

EXAMPLE IX

A water-in-oil cream composition was prepared in accordance with the procedure of Example V with 0.5 g monothioglycerol replacing the ascorbic acid and omitting the butylated hydroxytoluene. The composition consisted of the following ingredients:

| Ingredient | % w/w |
| --- | --- |
| mineral oil | 25.000 |
| hydroxyoctacosanyl hydroxystearate (Elfacos C26) | 5.000 |
| sorbitol solution, 70% | 5.000 |
| methoxy PEG-22/dodecyl glycol copolymer (Elfacos E200) | 5.000 |
| PEG-45/dodecyl glycol copolymer (Elfacos ST9) | 3.000 |
| stearoxytrimethylsilane | 1.000 |
| dimethicone (50 cstk) | 1.000 |
| Vitamin A alcohol (retinol)* | 0.345 |
| methylparaben | 0.300 |
| fragrance | 0.250 |
| propylparaben | 0.200 |
| Quaternium 15 (Dowicil 200) | 0.100 |
| disodium edetate | 0.100 |
| monothioglycerol | 0.050 |
| butyrated hydroxytoluene | 0.000 |
| ascorbic acid | 0.000 |
| 50% aqueous NaOH | q.s. to pH 4.7 |
| deionized water | q.s. to 100.000 |

*all-trans (USP)

The resulting water-in-oil emulsion composition was found to retain 92.8% of its original amount of retinol after 4 weeks aging at room temperature (21° C.), 92.8% after 4 weeks aging at 40° C., and 90.4% after 4 weeks aging at 50° C. The composition was found to retain 90.8% of its original level of retinol after 8 weeks aging at room temperature, 82.4% after 8 weeks aging at 40° C., and 65.3% after 8 weeks aging at 50° C. The composition was found to retain 80% of its original level of retinol after 13 weeks aging at room temperature, 62.3% after 13 weeks aging at 40° C., and 65.7% after 13 weeks aging at 50° C.

EXAMPLE X

A water-in-oil cream composition was prepared in accordance with the procedure of Example V with 1.0 g sodium metabisulfite replacing the ascorbic acid and consisted of the following ingredients:

| Ingredient | % w/w |
| --- | --- |
| mineral oil | 25.000 |
| hydroxyoctacosanyl hydroxystearate (Elfacos C26) | 5.000 |
| sorbitol solution, 70% | 5.000 |
| methoxy PEG-22/dodecyl glycol copolymer (Elfacos E200) | 5.000 |
| PEG-45/dodecyl glycol | 3.000 |

| Ingredient | % w/w |
| --- | --- |
| copolymer (Elfacos ST9) | |
| stearoxytrimethylsilane | 1.000 |
| dimethicone (50 cstk) | 1.000 |
| Vitamin A alcohol (retinol)* | 1.250 |
| methylparaben | 0.300 |
| fragrance | 0.250 |
| propylparaben | 0.200 |
| Quaternium 15 (Dowicil 200) | 0.100 |
| disodium edetate | 0.100 |
| sodium metabisulfite | 0.100 |
| butylated hydroxytoluene | 0.100 |
| ascorbic acid | 0.000 |
| 50% aqueous NaOH | q.s. to pH 4.7 |
| deionized water | q.s. to 100.000 |

*all-trans (USP)

After 13 weeks aging, the composition was found to retain 96% of its original level of retinol.

EXAMPLE XI

A water-in-oil cream composition was prepared in accordance with the procedure of Example V with 0.5 g sodium formaldehyde sulfoxylate replacing the ascorbic acid and omitting the butylated hydroxytoluene. The composition consisted of the following ingredients:

| Ingredient | % w/w |
| --- | --- |
| mineral oil | 25.000 |
| hydroxyoctacosanyl hydroxystearate (Elfacos C26) | 5.000 |
| sorbitol solution, 70% | 5.000 |
| methoxy PEG-22/dodecyl glycol copolymer (Elfacos E200) | 5.000 |
| PEG-45/dodecyl glycol copolymer (Elfacos ST9) | 3.000 |
| stearoxytrimethylsilane | 1.000 |
| dimethicone (50 cstk) | 1.000 |
| Vitamin A alcohol (retinol)* | 0.375 |
| methylparaben | 0.300 |
| fragrance | 0.250 |
| propylparaben | 0.200 |
| Quaternium 15 (Dowicil 200) | 0.100 |
| disodium edetate | 0.100 |
| sodium formaldehyde sulfoxylate | 0.050 |
| butylated hydroxytolurne | 0.000 |
| ascorbic acid | 0.000 |
| 50% aqueous NaOH | q.s. to pH 4.7 |
| deionized water | q.s. to 100.000 |

*all-trans (USP)

The resulting water-in-oil emulsion composition was found to retain 92.4% of its original amount of retinol after 4 weeks aging at room temperature (21° C.), 98% after 4 weeks aging at 40° C., and 92% after 4 weeks aging at 50° C. The composition was found to retain 84.4% of its original level of retinol after 8 weeks aging at room temperature, 84.4% after 8 weeks aging at 40° C. and 75.7% after 8 weeks aging at 50° C. The composition was found to retain 80% of its original level of retinol after 13 weeks aging at room temperature, 72.5% after 13 weeks aging at 40° C., and 72.1% after 13 weeks aging at 50° C.

EXAMPLE XII

A water-in-oil cream composition was prepared in accordance with the procedure of Example V with 0.5 g 1,4 diazobicyclo-(2,2,2)-octane replacing the ascorbic acid and omitting the butylated hydroxytoluene. The composition consisted of the following ingredients:

| Ingredient | % w/w |
| --- | --- |
| mineral oil | 25.000 |
| hydroxyoctacosanyl hydroxystearate (Elfacos C26) | 5.000 |
| sorbitol solution | 5.000 |
| methoxy PEG-22/dodecyl glycol copolymer (Elfacos E200) | 5.000 |
| PEG-45/dodecyl glycol copolymer (Elfacos ST9) | 3.000 |
| stearoxytrimethylsilane | 1.000 |
| dimethicone (50 cstk) | 1.000 |
| Vitamin A alcohol (retinol)* | 0.375 |
| methylparaben | 0.300 |
| fragrance | 0.250 |
| propylparaben | 0.200 |
| Quaternium 15 (Dowicil 200) | 0.100 |
| disodium edetate | 0.100 |
| 1,4-diazobicyclo-(2,2,2)-octane | 0.050 |
| butylated hydroxytoluene | 0.000 |
| ascorbic acid | 0.000 |
| 50% aqueous NaOH | q.s. to pH 4.7 |
| deionized water | q.s. to 100.000 |

*all-trans (USP)

The resulting water-in-oil emulsion composition was an off-white cream and was found to retain 91.8% of its original amount of retinol after 13 weeks aging at room temperature (21° C.).

The following Examples illustrate still further embodiments of the present invention.

EXAMPLE XIII

A water-in-oil cream composition was prepared in accordance with the procedure of Example V and consisted of the following ingredients:

| Ingredient | % w/w |
| --- | --- |
| mineral oil | 25.000 |
| hydroxyoctacosanyl hydroxystearate (Elfacos C26) | 5.000 |
| sorbitol solution, 70% | 5.000 |
| methoxy PEG-22/dodecyl glycol copolymer (Elfacos E200) | 5.000 |
| PEG-45/dodecyl glycol copolymer (Elfacos ST9) | 3.000 |
| stearoxytrimethylsilane | 1.000 |
| dimethicone (50 cstk) | 1.000 |
| Vitamin A alcohol (retinol)* | 0.125 |
| methylparaben | 0.300 |
| fragrance | 0.250 |
| propylparaben | 0.200 |
| Quaternium 15 (Dowicil 200) | 0.100 |
| disodium edetate | 0.100 |
| sodium bisulfite | 0.100 |
| butylated hydroxytoluene | 0.100 |
| 50% aqueous NaOH | q.s. to pH 4.7 |
| deionized water | q.s. to 100.000 |

*all-trans (USP)

The resulting water-in-oil emulsion was an off white cream.

EXAMPLE XIV

A water-in-oil cream composition was prepared in accordance with the procedure of Example V with the addition of 20 g silicon dioxide to the phase containing the mineral oil and consisted of the following ingredients:

| Ingredient | % w/w |
| --- | --- |
| mineral oil | 25.000 |
| hydroxyoctacosanyl hydroxystearate (Elfacos C26) | 6.000 |
| sorbitol solution, 70% | 5.000 |
| methoxy PEG-22/dodecyl glycol copolymer (Elfacos E200) | 5.000 |
| PEG-45/dodecyl glycol copolymer (Elfacos ST9) | 3.000 |
| silicon dioxide | 2.000 |
| stearoxytrimethylsilane | 1.000 |
| dimethicone (50 cstk) | 1.000 |
| Vitamin A alcohol (retinol)* | 0.345 |
| methylparaben | 0.300 |
| fragrance | 0.250 |
| propylparaben | 0.200 |
| Quaternium 15 (Dowicil 200) | 0.100 |
| disodium edetate | 0.100 |
| ascorbic acid | 0.100 |
| butylated hydroxytoluene | 0.050 |
| 50% aqueous NaOH | q.s. to pH 4.7 |
| deionized water | q.s. to 100.000 |

*all-trans (USP)

The resulting water-in-oil emulsion composition was an off-white cream.

EXAMPLE XV

A retinol cream composition was prepared according to the following procedure. In a suitable sized glass beaker blanketed with argon gas and fitted with a stainless steel stirrer 10 g PVP/Eicosene Copolymer, 5 g Phenoxyethanol, 2.45 g Polysorbate 20, 1.54 g Dimethicone, 10 g Arlacel 481, 25 g PEG-7 Hydrogenated Castor Oil, 15 g C12–15 Alcohols Benzoate, 85 g Cetearyl Octanoate, 20 g Silicon Dioxide, and 0.25 g BHT were heated to 80° C. and mixed. In a separate glass container, also blanketed with argon gas and fitted with a stainless steel stirrer, approximately 325 g Purified Water USP, 0.5 g Ascorbic Acid, 0.5 g Disodium EDTA and 1.5 g Xanthan Gum were mixed, adjusted to pH 4.7 with dilute sodium hydroxide Q.S., heated to 80° C. and added to the first mixture with agitation to form a water-in-oil emulsion. The emulsion was homogenized to further refine the particle size and was cooled to about 50° C. with ordinary mixing. 0.25 g Fragrance and 0.9285 g Retinol were added and Purified Water was added to return the batch weight to 500 g. The batch was mixed until uniform and the temperature was about 40° C. The finished batch was filled into blind-end aluminum tubes under argon blanketing. The composition was a smooth, off-white cream and has the following formulation:

| Ingredient | % w/w |
| --- | --- |
| Purified Water, q.s. | 100.00 |
| C12–15 Alcohols Benzoate (Finsolv TN) | 3.00 |
| PEG-7 Hydrogenated Castor Oil (Arlacel 989) | 5.00 |
| Silicon Dioxide (Cab-O-Sil M5) | 4.00 |
| Cetearyl Octanoate (Crodamol CAP) | 17.00 |
| Arlacel 481 | 2.00 |
| PVP/Eicosene Copolymer (Ganex V 220) | 2.00 |
| Phenoxyethanol (Emeressence 1160) | 1.00 |
| Polysorbate 20 (Tween 21) | 0.49 |
| Dimethicone 50 cstk | 0.308 |
| Xanthan Gum (Keltrol) | 0.30 |
| Retinol (all-trans), USP | 0.1857 |
| Ascorbic Acid | 0.10 |
| EDTA Na$_2$ | 0.10 |

-continued

| Ingredient | % w/w |
| --- | --- |
| NaOH | 0.05 |
| BHT | 0.05 |
| Fragrance | 0.05 |

Various other features and embodiments of the present invention not specifically enumerated will be obvious to those skilled in the art, all of which may be achieved without departing from the spirit and the scope of the invention as defined by the following claims.

What is claimed is:

1. A skin care composition comprising a water-in-oil emulsion and a retinoid selected from the group consisting of Vitamin A alcohol, Vitamin A aldehyde, retinyl acetate, retinyl palmitate and mixtures thereof, said composition further comprising a stabilizing system comprising a chelating agent and at least one water-soluble antioxidant said composition retaining at least about 60% by weight of said retinoid after 13 weeks storage at 40° C.

2. The skin care composition of claim 1 wherein the retinoid is Vitamin A alcohol.

3. The skin care composition of claim 1 wherein the water-soluble antioxidant is selected from the group consisting of ascorbic acid, sodium sulfite, sodium metabisulfite, sodium bisulfite, sodium thiosulfite, sodium formaldehyde sulfoxylate, isoascorbic acid, thioglycerol, thiosorbitol, thiourea, thioglycolic acid, cysteine hydrochloride, 1,4-diazobicyclo-(2,2,2)-octane and mixtures thereof.

4. The skin care composition of claim 3 wherein the water-soluble antioxidant is selected from the group consisting of ascorbic acid, sodium bisulfite, sodium metabisulfite, thioglycerol, sodium formaldehyde sulfoxylate and 1,4-diazobicycle-(2,2,2,)-octane and mixtures thereof.

5. The skin care composition of claim 4 wherein the water-soluble antioxidant is ascorbic acid.

6. The skin care composition of claim 1 wherein the chelating agent is selected from the group consisting of ethylenediamine tetracetic acid (EDTA) and derivatives and salts thereof, dihydroxyethyl glycine, citric acid, tartaric acid, and mixtures thereof.

7. The skin care composition of claim 6 wherein the chelating agent is selected from the group consisting of ethylenediamine tetracetic acid and derivatives and salts thereof.

8. A skin care composition comprising a water-in-oil emulsion and a retinoid selected from the group consisting of retinol, retinal, retinyl acetate, retinyl palmitate and mixtures thereof, said composition further comprising a stabilizing system comprising a chelating agent and at least one water-soluble antioxidant, said composition retaining at least about 60% of said retinoid after 13 weeks storage at 40° C.

9. The skin care composition of claim 8 wherein the retinoid is Vitamin A alcohol.

10. The skin care composition of claim 8 wherein the water-soluble antioxidant is selected from the group consisting of ascorbic acid, sodium sulfite, sodium metabisulfite, sodium bisulfite, sodium thiosulfite, sodium formaldehyde sulfoxylate, isoascorbic acid, thioglycerol, thiosorbitol, thiourea, thioglycolic acid, cysteine hydrochloride, 1,4-diazobicyclo-(2,2,2)-octane and mixtures thereof.

11. The skin care composition of claim 10 wherein the water-soluble antioxidant is selected from the group consisting of ascorbic acid, sodium bisulfite, sodium metabisulfite, thioglycerol, sodium formaldehyde sulfoxylate and 1,4-diazobicyclo-(2,2,2,)-octane and mixtures thereof.

12. The skin care composition of claim 11 wherein the water-soluble antioxidant is ascorbic acid.

13. The skin care composition of claim 10 wherein the chelating agent is selected from the group consisting of ethylenediamine tetracetic acid (EDTA) and derivatives and salts thereof, dihydroxyethyl glycine, citric acid, tartaric acid, and mixtures thereof.

14. The skin care composition of claim 13 wherein the chelating agent is selected from the group consisting of ethylenediamine tetracetic acid and derivatives and salts thereof.

15. The skin care composition of claim 10 wherein said stabilizing system comprises a chelating agent and antioxidant present in each of the oil and water phases of said emulsion.

* * * * *